United States Patent
Mogorosi et al.

(10) Patent No.: US 9,533,923 B2
(45) Date of Patent: Jan. 3, 2017

(54) OLIGOMERISATION OF ETHYLENE TO MIXTURES OF 1-HEXENE AND 1-OCTENE

(71) Applicant: SASOL TECHNOLOGY (PROPRIETARY) LIMITED, Rosebank (ZA)

(72) Inventors: Moses Mokgolela Mogorosi, Sasolburg (ZA); Munaka Christopher Maumela, Sasolburg (ZA); Matthew James Overett, Johannesburg (ZA)

(73) Assignee: Sasol Technology (Proprietary) Limited, Rosebank (ZA)

( * ) Notice: Subject to any disclaimer, the term of this patent is extended or adjusted under 35 U.S.C. 154(b) by 0 days.

(21) Appl. No.: 14/888,717

(22) PCT Filed: May 6, 2014

(86) PCT No.: PCT/IB2014/061233
§ 371 (c)(1),
(2) Date: Nov. 3, 2015

(87) PCT Pub. No.: WO2014/181248
PCT Pub. Date: Nov. 13, 2014

(65) Prior Publication Data
US 2016/0083312 A1 Mar. 24, 2016

(30) Foreign Application Priority Data

May 9, 2013 (ZA) ................................ 2013/03374

(51) Int. Cl.
*C07C 2/00* (2006.01)
*C07C 2/32* (2006.01)
*C07C 2/36* (2006.01)

(52) U.S. Cl.
CPC . *C07C 2/32* (2013.01); *C07C 2/36* (2013.01); *C07C 2531/14* (2013.01); *C07C 2531/18* (2013.01); *C07C 2531/24* (2013.01); *C07C 2531/34* (2013.01)

(58) Field of Classification Search
CPC .......... C07C 2/32; C07C 2/36; C07C 2531/14; C07C 2531/18; C07C 2531/24; C07C 2531/34
See application file for complete search history.

(56) References Cited

U.S. PATENT DOCUMENTS

2006/0229480 A1* 10/2006 Blann et al. ........... B01J 31/143
585/535
2010/0190939 A1* 7/2010 Fritz et al. ............. B01J 31/143
526/126
2016/0083311 A1* 3/2016 Maumela et al. ........ C07C 2/36
585/513

FOREIGN PATENT DOCUMENTS

| WO | 02/03119 A1 | 1/2002 |
| WO | 2008/088178 A1 | 7/2008 |
| WO | 2011/140629 A1 | 11/2011 |
| WO | 2012/071644 A1 | 6/2012 |

OTHER PUBLICATIONS

Van Leeuwen et al., "New processes for the selective production of 1-octene", Coordination of Chemistry Reviews, vol. 255, No. 13, Oct. 4, 2010, pp. 1499-1517.

* cited by examiner

*Primary Examiner* — Nathan M Nutter
(74) *Attorney, Agent, or Firm* — Whitham, Curtis & Cook, P.C.

(57) ABSTRACT

A process for the oligomerization, preferably the tetramerization, of ethylene to predominantly 1-hexene or 1-octene or mixtures of 1-hexene and 1-octene includes contacting ethylene with a catalyst under ethylene oligomerization conditions. The catalyst comprises a source of chromium, a diphosphine ligating compound, and optionally an activator. The diphosphine ligating compound includes at least one substituted aromatic ring bonded to a phosphorous atom. The substituted aromatic ring is substituted at a ring atom adjacent to the ring atom bonded to the respective phosphorous atom with a group Y, where Y is of the form —$AR^{EWG}$, A being O, S or $NR^5$, where $R^5$ is a hydrocarbyl, heterohydrocarbyl or organoheteryl group, and $R^{EWG}$ is an electron withdrawing group.

15 Claims, No Drawings

OLIGOMERISATION OF ETHYLENE TO MIXTURES OF 1-HEXENE AND 1-OCTENE

TECHNICAL FIELD

This invention relates to the oligomerisation of ethylene to mixtures of predominantly 1-hexene and 1-octene, in particular in the presence of an activated chromium catalyst with novel diphosphine ligands

BACKGROUND OF THE INVENTION

It is known that chromium-based catalyst systems with diphosphine ligands catalyse the selective conversion of ethylene to 1-hexene and/or 1-octene depending on the reaction conditions and choice of ligand structure. In particular, the nature and position of any substituents on the aryl rings connected to the phosphines are crucial influences on the selectivity split between 1-hexene and 1-octene. Of particular interest to industry are catalysts for ethylene tetramerisation, as these catalysts are relatively rare. Octene is a valuable co-monomer for the production of high performance linear low density polyethylenes and elastomers, and few selective on-purpose routes to this chemical are known in industry. By comparison, catalysts for ethylene trimerisation are relatively common, and are used industrially by several companies. By tetramerisation it is meant that at least 30% 1-octene is produced in the process. By trimerisation it is meant that more than 70% 1-hexene is produced.

Non-limiting examples of selective ethylene tetramerisation catalyst systems include the ubiquitous Cr/bis(phosphino)amine (i.e. 'PNP') systems, particularly of the type $(Ar^1)(Ar^2)PN(R)P(Ar^3)(Ar^4)$, where $Ar^1$ to $Ar^4$ are aryl groups such as phenyl and R is a hydrocarbyl or a heterohydrocarbyl group, beginning with PNP ligands containing no substituents on the phenyl rings bonded to the P-atoms (e.g. as described in WO 2004/056479) and those with m- or p-methoxy groups on the phenyl rings (e.g. as described in WO 2004/056480). In addition to this, PNP systems containing o-fluoro groups on the phenyl rings are described in US 2008/0242811 and US 2010/0081777, and PNP systems bearing pendant donor atoms on the nitrogen linker are described in WO 2007/088329. Multi-site PNP ligands are discussed in US 2008/0027188. In addition to the Cr/PNP systems, chromium systems bearing N,N-bidentate ligands (e.g. as described in US 2006/0247399) can be used. PNP ligands with alkylamine or phosphinoamine groups bonded to one of the PNP phosphines (i.e. 'PNPNH' and 'PNPNP' ligands) are described in WO 2009/006979. Finally, carbon bridged diphosphine (i.e. 'PCCP' ligands) are described in WO 2008/088178 and WO 2009/022770.

Related ethylene trimerisation catalysts with high selectivity for 1-hexene can be obtained by using PNP ligands with ortho-methoxy or Ortho-alkyl substituents on the phenyl rings bonded to the P-atoms (e.g. as described in WO2002/04119, WO2004/056477 and WO2010/034101).

The above catalyst systems suffer from a number of shortcomings. These include low catalyst activity and high polymer co-product formation, particularly when operated at elevated temperatures, especially above 80° C. Many of these catalysts also suffer from high selectivity towards heavy oligomers (C10 to C30+ olefins). These problems are especially evident for tetramerisation catalysts, where the challenge of obtaining good catalyst performance together with good selectivity towards 1-octene at high reaction temperatures is severe.

In a recent review article describing catalyst systems for ethylene tetramerisation, van Leeuwen at al (Coordination Chemistry Reviews, 255, (2011), 1499-1517) have discussed the problems associated with elevated reaction temperatures. They state that: "In general the selective ethylene tetramerisation experiments are performed in the temperature range 40-60° C. Various studies on both semi-batch and continuous miniplant have shown a strong dependency of the reaction temperature on the activity and selectivity of the $Cr(III)/Ph_2N(R)PPh_2/MAO$ catalytic system. High reaction temperatures (>60° C.) significantly reduced the catalyst productivity as compared to reactions performed at lower temperature under the same ethylene pressure. Consequently catalyst decomposition with increasing temperature is probably the main reason for lower productivities at high temperatures."

When carrying out a process for tetramerisation of ethylene, the aim is to choose a catalyst system and adjust process conditions in order to produce the maximum amount of 1-octene, as opposed to trimerisation processes where catalysts and process conditions are adjusted to produce the maximum amount of 1-hexene. 1-Hexene is also typically co-produced in a tetramerisation process and it is well known in the art of the invention that higher temperatures shift the selectivity from 1-octene towards 1-hexene.

Furthermore, the formation of a high molecular weight polymer co-product by the Cr-based ethylene tetramerisation catalyst may present a major technical challenge when commercialising an ethylene tetramerisation process as polymer fouling reduces plant run time and necessitates shut-downs due to blockages and difficult temperature control. When running tetramerisation processes at reaction temperatures in the range of 40 to 80° C., the polymer precipitates out of solution in the reactor, which brings risk to the process due to the possibility of reactor or downstream equipment fouling.

Consequently, new catalyst systems which can operate with good rates, low polymer formation, good 1-octene to 1-hexene ratios and reduced selectivity to heavy oligomers are highly desirable. Such catalysts would be useful at oligomerisation temperatures of 40 to 80° C., by reducing the amount of unwanted co-products formed, including polyethylene and heavy oligomers. Alternatively, they could be useful at higher oligomerisation reaction temperatures, where the polymer co-product remains in solution, but where catalyst stability and adequate selectivity to 1-octene are the greatest challenges.

SUMMARY OF THE INVENTION

According to one aspect of the invention there is provided a process for the oligomerisation of ethylene to predominantly 1-hexene or 1-octene or mixtures of 1-hexene and 1-octene, the process including contacting ethylene with a catalyst under ethylene oligomerisation conditions, said catalyst comprising:
  i) a source of chromium;
  ii) a ligating compound of the formula

wherein $P^1$ and $P^2$ are phosphorus atoms;
X is a linking group between $P^1$ and $P^2$; and
$R^1$ to $R^4$ are independently a hydrocarbyl group, an organoheteryl group or a heterohydrocarbyl group, wherein at least one of $R^1$, $R^2$, $R^3$, and $R^4$ includes a substituted aromatic ring directly bonded to $P^1$ or $P^2$ and which is substituted at a ring atom adjacent to the ring atom bonded to $P^1$ or $P^2$ with a substituent Y, where Y can be represented as:

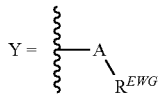

such that A is selected from the group consisting of O, S and $NR^5$, where $R^5$ is a hydrocarbyl, heterohydrocarbyl or organoheteryl group; and
$R^{EWG}$ is an electron withdrawing group; and
iii) optionally a catalyst activator or combination of catalyst activators.

DETAILED DESCRIPTION OF EMBODIMENTS OF THE INVENTION

The invention relates to a process for the oligomerisation, preferably the tetramerisation, of ethylene to predominantly 1-hexene or 1-octene or mixtures of 1-hexene and 1-octene, the process including contacting ethylene with a catalyst under ethylene oligomerisation conditions, said catalyst comprising a source of chromium; a diphosphine ligating compound, which compound includes at least one substituted aromatic ring bonded to a phosphorous atom, said substituted aromatic ring being substituted at a ring atom adjacent to the ring atom bonded to the respective phosphorous atom with a group Y, where Y is of the form —$AR^{EWG}$, A being O, S or $NR^5$, where $R^5$ is a hydrocarbyl, heterohydrocarbyl or organoheteryl group, and $R^{EWG}$ being an electron withdrawing group; and optionally an activator.

In the specification, the following definitions apply:

A "hydrocarbyl group" as per IUPAC includes a univalent group formed by removing one hydrogen atom from a hydrocarbon;

A "heterohydrocarbyl group" as defined herein is a univalent group formed by removing one hydrogen atom from a carbon atom of a heterohydrocarbon, that is a hydrocarbon compound which includes at least one hetero atom (that is, not being H or C), and which group covalently bonds with one other moiety through the resultant free valency on that carbon atom;

An "organoheteryl group" as per IUPAC includes univalent groups containing carbon, which are thus organic, but which have their free valence at an atom other than carbon;

A "hydrocarbylene group" as per IUPAC includes divalent groups formed by removing two hydrogen atoms from a hydrocarbon, the free valencies of which are not engaged in a double bond;

A "heterohydrocarbylene group" as defined herein is a divalent group formed by removing two hydrogen atoms from either one or two carbon atoms of an is organic molecule containing at least one heteroatom, the free valencies of which are not engaged in a double bond.

Chromium Source (i):

Any source of chromium that allows the oligomerisation to proceed may be used. The source of chromium may be an inorganic salt, an organic salt, a coordination compound or an organometallic complex.

In some embodiments the source of chromium is selected from the group consisting of chromium trichloride tristetrahydrofuran complex; (benzene)tricarbonyl chromium; chromium (III) octanoate; chromium hexacarbonyl; chromium (III) acetylacetonate; chromium (III) naphthenate; chromium (III) 2-ethylhexanoate; chromium (III) acetate; chromium (III) 2,2,6,6-tetramethylheptadionate; and chromium (III) chloride. In some embodiments it is chromium (III) acetylacetonate or chromium (III) 2-ethylhexanoate.

The chromium source may be introduced to the process as a coordination complex of the ligating compound. However, for reasons of cost and commercial operability, in some embodiments the ligating compound and chromium source are added as separate components to the process. Catalyst systems which give good catalyst performance only when an isolable chromium-ligand coordination complex is used therefore suffer a disadvantage to catalyst systems which can be prepared by mixing a chromium source and ligand in the process.

Ligating Compound (H):

Linking Group X

X may be selected from the group consisting of an organic linking group such as a hydrocarbylene, heterohydrocarbylene; an inorganic linking group comprising either a single- or two-atom linker spacer; and a group comprising dimethylmethylene, ethane-1,2-diyl, ethene-1,2-diyl, propane-1,2-diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracenediyl, 1,2-catecholate, 1,2-diarylhydrazine-1,2-diyl (—N(Ar)—N(Ar)— where Ar is an aryl group), 1,2-dialkylhydrazine-1,2-diyl (—N(Alk)-N(Alk)- where Alk is an alkyl or a cycloalkyl group), 1-alkyl-2-arylhydrazine-1,2-diyl (—N(Alk)-N(Ar)— where Alk is an alkyl or a cycloalkyl group and Ar is an aryl group), —N(R')—$X^1$—N(R")— where R' and R" are independently alkyl, cycloalkyl or aryl groups and $X^1$ is a hydrocarbylene group, —$B(R^5)$—, —$Si(R^5)_2$—, —$P(R^5)$— and —$N(R^5)$— where $R^5$ is hydrogen, a hydrocarbyl group, an organoheteryl group or a heterohydrocarbyl group. Preferably $R^5$ is a hydrocarbyl group or a heterohydrocarbyl group.

In some embodiments X consists of —$N(R^6)$—, —$N(R^6)$—$N(R^7)$—, —$C(R^{8a})(R^{8b})$—$N(R^6)$— or a hydrocarbylene, where $R^6$ and $R^7$ are independently a hydrocarbyl group, a heterohydrocarbyl group or an organoheteryl group, and $R^{8a}$ and $R^{8b}$ are independently a hydrogen, a hydrocarbyl group, a heterohydrocarbyl group or an organoheteryl group. In some embodiments $R^6$, $R^7$, $R^{8a}$ and $R^{8b}$ may be an alkyl, cycloalkyl, substituted alkyl, substituted cycloalkyl, aryl, substituted aryl, aryloxy, substituted aryloxy, alkoxycarbonyl, carbonyloxy, alkoxy, aminocarbonyl, carbonylamino, dialkylamino, pyrolyl, silyl group or derivative thereof, and aryl substituted with any of these substituents, and $R^{8a}$ and $R^{8b}$ may additionally be hydrogen. In some embodiments $R^6$, $R^7$, $R^{8a}$ and $R^{8b}$ may be an alkyl, cycloalkyl, substituted alkyl, substituted cycloalkyl, aryl, substituted aryl, and $R^{8a}$ and $R^{8b}$ may additionally be hydrogen. In some embodiments, $R^6$, $R^7$, $R^{8a}$ and $R^{8b}$ consist of hydrocarbyl groups, such as methyl, ethyl, propyl, allyl, isopropyl, cyclopropyl, butyl, tertiary-butyl, sec-butyl, cyclobutyl, pentyl, isopentyl, 1,2-dimethylpropyl (3-methyl-2-butyl), 1,2,2-trimethylpropyl (RIS-3,3-dimethyl-2-butyl), 1-(1-methylcyclopropyl)-ethyl, neopentyl, cyclopentyl, cyclohexyl, hexyl, cycloheptyl, cyclo-octyl, decyl, cyclodecyl, 1,5-dimethylheptyl, 1-methylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethylcyclohexyl, exo-2-norbornanyl, (1,1'-bis(cyclohexyl)-4,4'-methylene), 1,6-hexylene, 1-naphthyl, 2-naphthyl, diphenylmethyl, 1,2-diphenyl-ethyl, phenylethyl, 2-methylphenyl, 3-methylphenyl, 4-methylphenyl, 2,6-dimethyl-phenyl, or a 1,2,3,4-tetrahydronaphthyl, and $R^{8a}$ and $R^{8b}$ may additionally be hydrogen.

In a preferred embodiment X is a hydrocarbylene, —N($R^5$)—, —N($R^5$)—N($R^6$)—, —N($R^5$)—C($R^7$)($R^6$)—, N($R^5$)—$X^1$—N($R^6$) where $R^5$ and $R^6$ are independently a hydrocarbyl group, an organoheteryl group or a heterohydrocarbyl group, $R^7$ and $R^9$ are independently a hydrogen, a hydrocarbyl group, an organoheteryl group or a heterohydrocarbyl group, and $X^1$ is a hydrocarbylene group.

In some embodiments, X is —N($R^9$)—, where $R^9$ is a hydrocarbyl group, a heterohydrocarbyl group or an organoheteryl group. In some embodiments $R^9$ is a hydrocarbyl group or a heterohydrocarbyl group. In some embodiments $R^9$ is an alkyl, cycloalkyl or aryl group. In some embodiments $R^9$ is an alkyl or cycloalkyl group. In some embodiments $R^9$ is an alkyl group of the form —$CH_2R^{10}$, where $R^{10}$ is hydrogen or an alkyl group or a cycloalkyl group. In some embodiments $R^9$ is methyl or a linear alkyl group.

Nature of the Groups $R^1$-$R^4$ $R^1$ to $R^4$ are independently a hydrocarbyl, an organoheteryl group or a heterohydrocarbyl group, such that at least one of $R^1$, $R^2$, $R^3$, and $R^4$ includes a substituted aromatic ring directly bonded to $P^1$ or $P^2$, said substituted aromatic ring being substituted at the ring atom adjacent to the ring atom bonded to $P^1$ or $P^2$ with a group Y, where Y is of the form —$OR^{EWG}$ or —$SR^{EWG}$ or —$NR^5R^{EWG}$, $R^5$ being a hydrocarbyl, heterohydrocarbyl or organoheteryl group, and $R^{EWG}$ being an electron withdrawing group.

In some embodiments, $R^1$ to $R^4$ are independently hydrocarbyl or heterohydrocarbyl groups. In some embodiments $R^1$ to $R^4$ all include aromatic or heteroaromatic moieties directly bonded to $P^1$ or $P^2$. In some embodiments, at least one of the $R^1$ to $R^4$ groups is a substituted phenyl group and all of the remaining $R^1$ to $R^4$ groups are optionally substituted phenyl groups. Any of $R^1$ to $R^4$ that are not aromatic rings substituted at the ring atom adjacent to the ring atom bound to phosphorous by a group of the form Y as described in the paragraph above may be linked together, for example to form a dibenzophosphol-5-yl group together with either $P^1$ or $P^2$.

Nature of the Y-Substituted Aromatic Rings of the $R^1$-$R^4$ Groups

In some embodiments of the invention, the Y-substituted aromatic rings of the $R^1$ to $R^4$ groups are selected from a group consisting of phenyl, pyridyl, furyl, thiophenyl, imidazolyl, pyrazolyl and oxazolyl. In some embodiments, these substituted aromatic rings are selected from a group consisting of phenyl, pyridyl, furyl and thiophenyl. In some embodiments, these aromatic rings are phenyl groups, in which case the Y substituent will be at the ortho position relative to the carbon ring atom bonded to $P^1$ or $P^2$. In any of these embodiments, carbon ring atoms other than those bound to $P^1$ or $P^2$, or Y, may optionally be substituted with any univalent substituent, or be fused with further aromatic rings. Preferably, they are bonded to hydrogen atoms.

Nature of the Groups Y

The substituent Y, on the substituted aromatic rings of one or more of the $R^1$ to $R^4$, can be represented as:

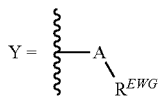

such that A is selected from the group consisting of O, S and $NR^5$, where $R^5$ is a hydrocarbyl, heterohydrocarbyl or organoheteryl group; and $R^{EWG}$ is an electron withdrawing group.

In some embodiments, A is O or S.

In some embodiments, A is O.

An electron withdrawing group is understood in the art to mean a substituent that by a mesomeric and/or inductive effect has the tendency to attract valence electrons from neighbouring atoms. In other words, such a group is electronegative with respect to neighbouring atoms, in other words in relation to the present invention to the A group. It thus causes a shift in the electron density from the remainder of the molecule towards itself, thereby reducing the electron density of the neighbouring group or remainder of the molecule. In particular, a univalent electron withdrawing group attracts electron density towards itself to a greater extent than would be caused by a hydrogen atom located at the same position.

A useful quantification of the level of electron-withdrawing capability is given by the Hammett sigma constants. The Hammett $\sigma_p$ value is a relative measurement comparing the electronic influence of the substituent in the para position of a phenyl ring to the electronic influence of a hydrogen substituted at the para position. This well known parameter is described in many references, for instance, C. Hansch, Chem. Rev. 1991, 91, 165-195; J. March, Advanced Organic Chemistry, John Wiley & Sons, 1992, 4$^{th}$ edition, page 278-286; H. Brown, J. Am. Chem. Soc. 1958, 4979-4987.

The Hammett $\sigma_p$ constant values (where $\sigma_p$ for —H is defined as 0) are negative for electron donating groups, e.g. $\sigma_p$=−0.57, −0.28 and −0.14 for —$NH_2$, —$OCH_3$ and —$CH_3$ respectively (March, page 280), and positive for electron-withdrawing groups, e.g. $\sigma_p$=+0.24, +0.70, +0.53 and +0.81 for —Cl, —CN, —$CF_3$ and —$NO_2$ respectively (March, page 280). Other known electron withdrawing substituents are aliphatic and aromatic acyl groups (—C[=O]—R), the aldehyde group (—C[=O]H), and sulfonyl groups (—$SO_2R$). In addition, a number of heterocyclic groups are electron withdrawing groups and have positive $\sigma_p$ values. For example, 2-pyridyl ($\sigma_p$=+0.17), 4-pyridyl ($\sigma_p$=+0.44), 3-pyridizinyl ($\sigma_p$=+0.48), 2-benzoxazolyl ($\sigma_p$=+0.33), 2-benzothiazolyl ($\sigma_p$=+0.29), 1-imidazolyl ($\sigma_p$=+0.18), tetrazole ($\sigma_p$=+0.58), and triazole ($\sigma_p$=+0.45) are electron withdrawing groups (C. Hansch, Chem. Rev. 1991, 91, 165-195 C. Janiak, Chem Eur, J. Chem 1996, 2 (8), 992-1000, F. Fülöp et al, J Heterocyclic Chem, 1997, 34, 289-293, A. Abbotto et al, J Org Chem, 1996, 61, 1770).

In some embodiments of the invention, $R^{EWG}$ is more electron withdrawing than a hydrogen atom substituent.

In some embodiments of the invention, $R^{EWG}$ has a positive $\sigma_p$ value, where $\sigma_p$ is the Hammett constant for a substituent's effect when located at the para-position of a phenyl ring. In some preferred embodiments, $R^{EWG}$ has a $\sigma_p$ value of greater than +0.15.

$R^{EWG}$ may be a divalent group that is bonded to Y and also bonded to another ring atom of the aromatic ring of which Y is a substituent, to form a cyclic structure.

In some embodiments, $R^{EWG}$ is selected from a group comprising halogen-substituted alkyl, halogen-substituted cycloalkyl, halogen-substituted aryl, heteroaryl, —$SO_2R^6$, —(C=O)$R^6$, —CN; where $R^6$ is a hydrogen, a hydrocarbyl group, or a heterohydrocarbyl group.

In some embodiments, $R^{EWG}$ is selected from a group comprising halogen-substituted alkyl, halogen-substituted cycloalkyl, heteroaryl, —(C=O)R⁶, and —CN; where R⁶ is a hydrogen, a hydrocarbyl group, or a heterohydrocarbyl group.

In some embodiments, $R^{EWG}$ is selected from a group comprising halogen-substituted alkyl, halogen-substituted cycloalkyl, halogen-substituted aryl and heteroaryl.

In some embodiments, $R^{EWG}$ is selected from a group comprising fluorine-substituted alkyl, fluorine-substituted cycloalkyl and fluorine-substituted aryl.

In some embodiments, $R^{EWG}$ is selected from a group comprising fluorine-substituted alkyl.

In some embodiments, $R^{EWG}$ is a fluorine-substituted alkyl such that at least one fluorine atom is bonded to the carbon atom bonded to A.

In some embodiments, $R^{EWG}$ is selected from a group comprising fluoromethyl; difluoromethyl; trifluoromethyl; 1,1'-difluoroethyl; chlorodifluoromethyl; pentafluoroethyl; heptafluoropropyl; nonafluorobutyl, and the like In some embodiments, $R^{EWG}$ is trifluoromethyl.

Number and Substitution Pattern of the Y-Substituted Aromatic $R^1$-$R^4$ Groups $R^1$ to $R^4$ are independently a hydrocarbyl, an organoheteryl group or a heterohydrocarbyl group, such that at least one of $R^1$, $R^2$, $R^3$, and $R^4$ includes a substituted aromatic ring directly bonded to $P^1$ or $P^2$, said substituted aromatic ring being substituted at the ring atom adjacent to the ring atom bonded to $P^1$ or $P^2$ with a group Y, where Y is of the form —$OR^{EWG}$, —$SR^{EWG}$ or $NR^5R^{EWG}$, $R^5$ being a hydrocarbyl, heterohydrocarbyl or organoheteryl group and $R^{EWG}$ being an electron withdrawing group. In some embodiments no more than two of $R^1$ to $R^4$ includes such a Y-substituted aromatic group. In some embodiments, $R^1$ and $R^2$ include such a Y-substituted aromatic group. In some embodiments, only one of $R^1$, $R^2$, $R^3$, and $R^4$ includes such a Y-substituted aromatic group.

Other Considerations

Any one of $R^1$ to $R^4$ may independently be linked to one or more of each other, or to X, to form a cyclic structure. $R^{EWG}$ may be linked to another atom of the Y-substituted aromatic ring, or to another $R^1$ to $R^4$ group to form a cyclic structure.

The ligating compound may also include multiple $R^1R^2P^1XP^2R^3R^4$ units. Non-limiting examples of such ligands include dendrimeric ligands as well as ligands where the individual units are coupled either via one or more of the $R^1$-$R^4$ groups or via the linking group X.

It will be appreciated that a diphosphinoimine compound of the form $R^1R^2P^1$—$P^2$(=$NR^9$)$R^3R^4$ ('P—P=N') is a rearranged isomer of the diphosphinoamine compound $R^1R^2P^1N(R^9)P^2R^3R^4$ ('P—N—P') claimed in the present invention, as shown by Dyson et al in Inorganica Chimica Acta 359 (2006) 2635-2643. Regardless of the structural formulation of the ligating compound in its pure and isolated form, its use will fall under the present invention if it exists in the 'P—N—P' form when used in a tetramerisation process.

In some embodiments the ligating compound may be one of:

(2-[trifluoromethoxy]phenyl)₂PN(i-propyl)P(phenyl)₂;
(2-[trifluoromethoxy]phenyl)(phenyl)PN(i-propyl)P(phenyl)₂;
(2-[trifluoromethoxy]phenyl)₂PN(i-butyl)P(phenyl)₂;
(2-[trifluoromethoxy]phenyl)(phenyl)PN(i-butyl)P(phenyl)₂;
(2-[trifluoromethoxy]phenyl)₂PN(n-butyl)P(phenyl)₂;
(2-[trifluoromethoxy]phenyl)(phenyl)PN(n-butyl)P(phenyl)₂;
(2-[trifluoromethoxy]phenyl)(phenyl)PN(n-butyl)P(2-[trifluoromethoxy]phenyl) (phenyl);
(2-[trifluoromethoxy]phenyl)₂PN(n-butyl)P(2-[trifluoromethoxy]phenyl)₂;
(2-[trifluoromethoxy]phenyl)₂PN(methyl)P(2-[trifluoromethoxy]phenyl)₂;
(2-[trifluoromethoxy]phenyl)₂PN(n-butyl)(dibenzophosphol-5-yl);
(2-[trifluoromethoxy]phenyl)(phenyl)PN (n-butyl)(dibenzophosphol-5-yl);
(2-[trifluoromethoxy]phenyl)₂PN (n-butyl)P(furan-2-yl)₂;
(2-[trifluoromethoxy]phenyl)(phenyl)PN(n-butyl)P(furan-2-yl)₂;
(2-[trifluoromethoxy]phenyl)₂PN(n-butyl)P(furan-3-yl)₂;
(2-[trifluoromethoxy]phenyl)(phenyl)PN (n-butyl)P(furan-3-yl)₂;
(2-[trifluoromethoxy]phenyl)₂PN(n-butyl)P(pyrid-2-yl)₂;
(2-[trifluoromethoxy]phenyl)(phenyl)PN (n-butyl)P(pyrid-2-yl)₂;
(2-[trifluoromethoxy]phenyl)₂PN (n-butyl)P(pyrid-3-yl)₂;
(2-[trifluoromethoxy]phenyl)(phenyl) PN (n-butyl)P(pyrid-3-yl)₂;
(2-[trifluoromethoxy]phenyl)₂PN(n-butyl)P(pyrid-4-yl)₂;
(2-[trifluoromethoxy]phenyl)(phenyl)PN (n-butyl)P(pyrid-4-yl)₂;
(2-[difluoromethoxy]phenyl)₂PN(i-propyl)P(phenyl)₂;
(2-[difluoromethoxy]phenyl)(phenyl)PN(i-propyl)P(phenyl)₂;
(2-[fluoromethoxy]phenyl)₂PN(i-propyl)P(phenyl)₂;
(2-[fluoromethoxy]phenyl)(phenyl)PN(i-propyl)P(phenyl)₂;
(2-[pentafluoroethoxy]phenyl)₂PN(i-propyl)P(phenyl)₂;
(2-[pentafluoroethoxy]phenyl)(phenyl)PN(i-propyl)P(phenyl)₂;
(2-[2',2',2'-trifluoroethoxy]phenyl)₂PN(i-propyl)P(phenyl)₂;
(2-[2',2',2'-trifluoroethoxy]phenyl)(phenyl)PN(i-propyl)P(phenyl)₂;
(2-[nonafluorobutoxy]phenyl)₂PN(i-propyl)P(phenyl)₂;
(2-[nonafluorobutoxy]phenyl)(phenyl)PN(i-propyl)P(phenyl)₂;
(2-[pentafluorophenoxy]phenyl)₂PN(i-propyl)P(phenyl)₂;
(2-[pentafluorophenoxy]phenyl)(phenyl)PN(i-propyl)P(phenyl)₂;
(2-[chlorodifluoromethoxy]phenyl)₂PN(i-propyl)P(phenyl)₂;
(2-[chlorodifluoromethoxy]phenyl)(phenyl)PN(i-propyl)P(phenyl)₂;
(2-[trichloromethoxy]phenyl)₂PN(i-propyl)P (phenyl)₂;
(2-[trichloromethoxy]phenyl)(phenyl)PN(i-propyl)P (phenyl)₂;
(2-[trifluoromethanesulfonyloxy]phenyl)₂PN(i-propyl)P(phenyl)₂;
(2-[trifluoromethanesulfonyloxy]phenyl)(phenyl)PN(i-propyl)P(phenyl)₂;
(2-[trifluoroacetoxy]phenyl)₂PN(i-propyl)P(phenyl)₂;
(2-[trifluoroacetoxy]phenyl)(phenyl)PN(i-propyl) P(phenyl)₂;
(2-[cyanato]phenyl)(phenyl)PN(n-butyl)P(phenyl)₂;
(2-[2-pyridyloxy]phenyl)(phenyl)PN(n-butyl)P(phenyl)₂;
(2-[3-pyridyloxy]phenyl)(phenyl)PN(n-butyl)P(phenyl)₂;
(2-[4-pyridyloxy]phenyl)(phenyl)PN(n-butyl)P(phenyl)₂;
(2-[2-benzothiazolyloxy]phenyl)(phenyl)PN(n-butyl)P(phenyl)₂;
(2-[trifluoromethoxy]phenyl)₂PN(Me)N(M e)P(phenyl)₂;
(2-[trifluoromethoxy]phenyl)(phenyl)PN(Me)N(Me)P(phenyl)₂;
(2-[trifluoromethoxy]phenyl)₂PN(Me)N(Me)(dibenzophosphol-5-yl);

(2-[trifluoromethoxy]phenyl)(phenyl)PN(Me)N(Me)(dibenzophosphol-5-yl);
(2-[trifluoromethoxy]phenyl)$_2$P(1,2-phenylene)P(phenyl)$_2$;
(2-[trifluoromethoxy]phenyl)(phenyl)P(1,2-phenylene)P(phenyl)$_2$;
(2-[trifluoromethoxy]phenyl)$_2$PCH$_2$N(napthyl)P(phenyl)$_2$;
(2-[trifluoromethoxy]phenyl)(phenyl)PCH$_2$N(napthyl)P(phenyl)$_2$;
(2-[trifluoromethoxy]phenyl)$_2$PN(methyl)CH$_2$CH$_2$CH$_2$CH$_2$N(methyl)P(phenyl)$_2$;
(2-[trifluoromethoxy]phenyl)(phenyl)PN(methyl)CH$_2$CH$_2$CH$_2$CH$_2$N(methyl)P(phenyl)$_2$.

Activator/Additives (iii):

The above process may include an activator to activate the catalyst. Such an activator is a compound that generates an active catalyst when the activator is combined with the catalyst. These activators may be the same or similar to those found to be useful for activating transition-metal-based olefin polymerisation catalysts, a review of which is provided by Marks [*Chem Rev.* 2000, 100, 1391-1394]. Mixtures of activators may also be used. Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminum compounds include compounds of the formula AlR$_3$, where each R is independently C$_1$-C$_{12}$ alkyl, oxygen or halide, and compounds such as LiAlH$_4$ and the like. Examples include trimethylaluminum (TMA), triethylaluminum (TEA), tri-isobutylaluminium (TIBA), tri-n-octyl-aluminium, methylaluminium dichloride, ethylaluminium dichloride, dimethylaluminium chloride, diethylaluminium chloride, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available aluminoxanes are generally believed to be mixtures of linear and cyclic compounds. The cyclic aluminoxanes can be represented by the formula [R$^{11}$AlO]$_s$ and the linear aluminoxanes by the formula R$^{12}$(R$^{13}$AlO)$_s$ wherein s is a number from about 2 to 50, and wherein R$^{11}$, R$^{12}$, and R$^{13}$ represent hydrocarbyl groups, typically C$_1$ to C$_6$ alkyl groups, for example methyl, ethyl or butyl groups. Alkylaluminoxanes especially methylaluminoxane (MAO) are particularly suitable. (MAO is also referred to as methalumoxane and methylalumoxane in the literature).

It will be recognized by those skilled in the art that commercially available alkylaluminoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylaluminoxane are generally quoted herein on a molar basis of aluminium (and include such "free" trialkylaluminium). The alkylaluminoxane and/or alkylaluminium may be added to the reaction media (i.e. ethylene and/or diluent and/or solvent) prior to the addition of the catalyst or at the same time as the catalyst is added. Such techniques are known in the art of oligomerization and are disclosed in more detail in for example, U.S. Pat. Nos. 5,491,272; 5,750,817; 5,856,257; 5,910,619; and 5,919,996 as well as WO 2008/146215 and WO 2007/007272.

In the preparation of the catalyst systems used in the present invention, the optimal quantity of activating compound to be employed is easily determined by simple testing, for example, by the preparation of small test samples which can be used to oligomerize small quantities of ethylene and thus to determine the activity of the produced catalyst. It is generally found for alkylaluminium and aluminoxane based activators or co-activators that a suitable quantity employed is 0.5 to 2000 moles of aluminium per mole of chromium.

Examples of suitable organoboron activator compounds are boroxines, NaBH$_4$, trimethylboron, triethylboron, triphenylboron, dimethylphenylammoniumtetra(phenyl)borate, trityltetra(phenyl)borate, dimethylphenylammonium tetrakis(pentafluorophenyl)borate, trityl tetrakis(pentafluorophenyl)borate, tris(pentafluorophenyl) boron, sodium tetrakis[(bis-3,5-trifluoromethyl)phenyl]borate, dimethylphenylammonium tetrakis[(bis-3,5-trifluoromethyl)phenyl]borate, and trityl tetrakis[(bis-3,5-trifluoromethyl)phenyl]borate.

Those skilled in the art will recognise that boron-containing activators are commonly used in combination with aluminium alkyl activators.

In some embodiments organoboron activators, as described in WO 2010/092554, include a cation and a non-coordinating anion of the general formula

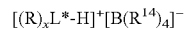

wherein:
L* is an atom selected from the group consisting of N, S and P;
the cation [(R)$_x$L*-H]$^+$ is a Bronsted acid;
x is an integer 1, 2 or 3;
each R is the same or different and each is a —H, hydrocarbyl group or a heterohydrocarbyl group;
provided that at least one of R comprises at least 6 carbon atoms and provided further that the total number of carbon atoms in (R)$_x$ collectively is greater than 12;
R$^{14}$ independently at each occurrence is selected from the group consisting of hydride, dialkylamido, halide, alkoxide, aryloxide, hydrocarbyl, halosubstituted-hydrocarbyl radicals, halosubstituted-alkoxide, halosubstituted-aryloxide and a halosubstituted aromatic moiety with at least one halide substituent on the aromatic moiety.

Illustrative, but non-limiting examples of these organoboron activators include methyldi(octadecyl)ammonium tetrakis(pentafluorophenyl) borate and trioctylammonium tetrakis(pentafluorophenyl) borate.

The source of chromium and the organoboron activator may be combined in proportions to provide organoboron compound/chromium molar ratios from about 0.1 to 50 organoboron to 1 chromium, or from about 0.8 to 20 organoboron to 1 chromium, or from 1 to 10 organoboron to 1 chromium.

In some embodiments activators, as described in WO 2007/039851, include a cation and an anion component, and may be represented by the following formula:

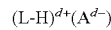

where L is a neutral Lewis base; H is hydrogen; (L-H)$^{d+}$ is a Bronsted acid; A$^{d-}$ is a non-coordinating anion having the charge d; and d is an integer from 1 to 3.

In these activator compounds, A$^{d-}$ can be a fluorinated aluminate group. Illustrative but non-limiting examples of the anion component A$^{d-}$ are [Al{OC(CF$_3$)$_3$}$_4$]$^-$; [Al(OC$_6$F$_5$)$_4$]$^-$; [Al(C$_6$F$_4$O$_2$)$_2$]$^-$; [AlF{OC(CF$_3$)$_3$}$_3$]$^-$; [Al$_2$F{OC(CF$_3$)$_3$}$_6$]$^-$; and [Ta(OC$_6$F$_5$)$_6$]$^-$.

The activator compound may optionally be a solid material, or be supported on an insoluble solid material. For example, aluminoxanes such as MAO and borate activators may be supported on inorganic oxides such as alumina, silica, $MgCl_2$ or the like.

The process may further include the use of compounds that may act as a reducing or oxidising agent, such as sodium or zinc metal and the like, or an oxygen-containing compound, for example oxygen and the like. Additionally, hydrogen ($H_2$) and/or silanes and the like may be used in the catalytic composition or otherwise added to the process. The process may also include the use of a zinc species as an additive, as described in WO 2011/048527, which is herein incorporated by reference. Preferred zinc species would be dialkyl zinc reagents such as dimethylzinc or diethylzinc.

Catalyst Preparation:

The chromium (i) and ligand (ii) may be present in any molar ratio which produces oligomer, and in some embodiments is between 100:1 and 1:100, or from 10:1 to 1:10, or from 3:1 to 1:3. Generally the amounts of (i) and (ii) are approximately equal, i.e. a ratio of between 1.5:1 and 1:1.5.

The ligand, chromium and activators of the catalyst system utilized in the present invention may be added together simultaneously or sequentially, in any order, and in the presence or absence of ethylene in any suitable solvent at any suitable concentration, so as to give an active catalyst. For example, the ligand, chromium, activators and ethylene may be contacted together simultaneously; or the ligand, chromium and activators may be added together simultaneously or sequentially in any order and then contacted with ethylene; or chromium and the ligand may be added together to form an isolable metal-ligand complex and then added to the activator and contacted with ethylene; or the ligand, chromium and activators/co-activators may be added together to form an isolable metal-ligand complex and then contacted with ethylene. Any or all of the chromium source, ligating compound and activator components utilized in the present invention can be unsupported or supported on a support material, for example silica, alumina, $MgCl_2$ or zirconia, or on a polymer, for example polyethylene, polypropylene, polystyrene or poly(aminostyrene).

Diluent:

The process of the present invention may be carried out in the presence or absence of an added diluent. In some embodiments of the invention the diluents include oligomerisation products e.g. 1-octene and/or 1-hexene, aliphatic and aromatic hydrocarbon solvents and halogenated-aromatic solvents such as chlorobenzene, dichlorobenzene, fluorobenzene and the like. In some embodiments the diluents are aliphatic hydrocarbon solvents including but not limited to Isopar™, iso-octane, cyclohexane, cyclopentane, methylcyclohexane, propane, isobutane, isopentane, neopentane, 2-methylpentane, or 3-methylpentane.

Alternatively the process can be conducted as a bulk process in which essentially neat reactant and/or product olefins serve as the dominant medium.

Process Conditions:

The oligomerisation reaction may take place at any suitable temperature to allow oligomerisation to proceed. Suitable temperatures may be from ° C. to 200° C. Preferred temperatures are dependent on the process conditions utilized.

In one embodiment, the oligomerisation is conducted under slurry phase conditions, which is herein taken to mean that a substantial portion of any polymer co-product is present in the solid phase, and not predominantly dissolved in the liquid reaction medium under the chosen reaction conditions.

Suitable temperatures to achieve this range from 0° C. to about 80° C., including from about 40° C. to about 80° C. Such process conditions may be chosen for optimal catalyst activity and selectivity.

In another embodiment, the oligomerisation is conducted under solution phase conditions, which is herein taken to mean that any polymer co-product remains substantially dissolved in the liquid reaction medium under the chosen reaction conditions. Suitable temperatures to achieve this range from above 80° C. to about 130° C. In some embodiments the temperature range is between 85° C. or 90° C. and 130° C., whilst in other embodiments the temperature range is between 85° C. or 90° C. and 110° C. Such process conditions may be chosen to reduce fouling of the reactor or other process equipment.

Surprisingly, the catalysts of the present invention have been found to offer benefits over other catalysts known in the art, under both slurry phase and solution phase conditions.

Under slurry phase conditions, the catalysts of the present invention have extremely high activities, low polymer co-product formation and/or reduced selectivities to unwanted heavy oligomers (C10+), while retaining good selectivity towards 1-octene, a particularly favoured product.

Under solution phase conditions, the catalysts of the present invention are found to be highly active, with low polymer formation, above 80° C. Even more surprisingly, these catalysts are still highly active, with low polymer formation, above 90° C. Not wishing to be bound by theory, the catalysts of the present invention are less susceptible to the thermally induced catalytic decomposition pathways, as discussed by van Leeuwen.

Suitable reaction pressures are from atmospheric to 800 atmospheres (bar), or from 5 atmospheres to 100 atmospheres, or from 40 to 100 atmospheres, or from 60 to 100 atmospheres. It was demonstrated that the negative effect of higher reaction temperatures on selectivity towards 1-octene can be reversed through the use of higher reaction pressures, together with the catalysts and reaction temperature ranges of the present invention.

There exist a number of options for the tetramerisation reactor including batch, semi-batch, and continuous operation. In some embodiments the process is a continuous process, in which case reactors utilizing both CSTR and plug flow behavior may be considered. There are different potential configurations as a subset of these two types of reactors. For example, CSTR type reactors include bubble columns, stirred tanks, loop reactors with single or two phases while plug flow reactors include fixed bed and homogeneous tubular types of varying residence times. As a further subset, reactors can be configured with different cooling options such as internal or external heat exchangers, interstage coolers, and cold feed heat removal amongst others. All configurations can be run in continuous or batch mode, and there is opportunity to configure the same reactor several times in series or use combinations of different reactor types and cooling techniques together to achieve the desired result.

For systems where tetramerisation takes place in the liquid phase, different mass transfer opportunities exist including jet loop mixing, bubble column sparging, tubular reactor multiple injections and pre-saturation of the feed material amongst others.

The reactor type selected may depend on factors such as heat removal, mechanical robustness with regard to fouling, residence time distributions, product composition effects as a result of secondary reactions and mechanical equipment cost implications. In a slurry phase process where polymer precipitates out of the reaction medium, the selection criteria of heat removal and mechanical robustness with regard to fouling may be expected to dominate and many reactor configurations may therefore be excluded. In a solution phase process, a wider range of reactor configurations may be considered and implemented to optimize factors such as residence time distributions, product composition effects as a result of secondary reactions and mechanical equipment cost implications. In particular, the use of reactors wherein reaction cooling is effected by means of heat exchangers in contact with the reaction medium may be practical in a solution phase process, whereas the susceptibility of such heat exchangers to fouling may rule out such options for a slurry-phase process.

The invention will now be described in more detail, by way of example only, with reference to the following non-limiting examples.

EXAMPLES

The following abbreviations are used in the examples:
PCl chlorophosphine, i.e. $R^1R^2$PCl, where $R^1$ and $R^2$ are hydrocarbyl or heterohydrocarbyl groups
nBu normal-butyl
iPr isopropyl
Ph phenyl
PNH phosphinoamine, e.g. $Ar_2$PN(R)H, where Ar is an aryl, and R is an organyl group
PNP bis phosphinoamine, e.g. $Ar_2$PN(R)P$Ar_2$, where Ar is an aryl, and R is an organyl group
DCM dichloromethane
THF tetrahydrofuran
TMP 2,2,4-trimethylpentane
MCH methylcyclohexane
MMAO-3A An aluminoxane product General Experimental Conditions for Ligand Synthesis All reactions were carried out under an argon atmosphere using a dual vacuum/nitrogen line and standard Schlenk techniques. Solvents were purified via an M-Braun solvent purification system. All reagents purchased from commercial suppliers were used without further purification. NMR spectra were recorded on a Varian 400 MHz spectrometer using CDCl$_3$. PNP compounds below were prepared by modification of the procedure described in *Synthesis*, 2007, 24, 3863.

Preparation of
(2-[trifluoromethoxy]phenyl)(phenyl)phosphine chloride

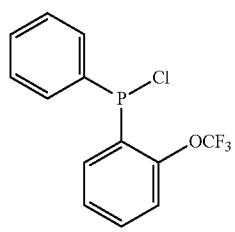 [SMILES: FC(F)(F)Oc1ccccc1P(Cl)c1ccccc1]

To a flame dried Schlenk tube containing magnesium turnings (0.15 g, 6.22 mmol) in anhydrous THF (7 ml) was added 1-bromo-2-[trifluoromethoxy]benzene (1.0 g, 4.14 mmol). An exothermic reaction ensued. Stirring was continued at room temperature. Once the reaction exotherm had dissipated, the reaction mixture was used in the next step as described below:

The Grignard reagent (separated from excess Mg) was incrementally added to a solution of PhPCl$_2$ (0.74 g, 4.14 mmol) in anhydrous THF (10 ml) at −78° C. Once addition was complete, the reaction was stirred at room temperature for a further 20 min after which the reaction was complete as judged by $^{31}$P NMR ($^{31}$P NMR (CDCl$_3$): δ 72.27 (m); 61.81 (m)). The product was used in the next step without further purification.

Preparation of (chloro)(phenyl) PN(nBu)P(phenyl)$_2$

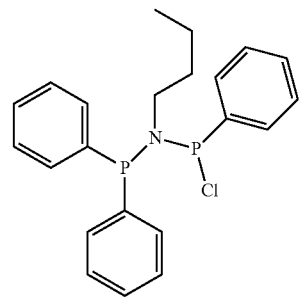 [SMILES: CCCCN(P(Cl)c1ccccc1)P(c1ccccc1)c1ccccc1]

PNH formation: To a stirred solution of excess n-butylamine (22.4 ml, 227.1 mmol) in diethyl ether (100 ml) at 0° C. was added Ph$_2$PCl (4.2 ml, 22.7 mmol) dropwise. After complete addition of Ph$_2$PCl, triethylamine (6.3 ml, 45.3 mmol) was added and the reaction was left to warm up to room temperature. The reaction mixture was filtered through a short alumina column and the volatiles (solvent and unreacted amine) were removed in vacuo to give the desired PNH, Ph$_2$PN(nBu)H, which was used in the next step (below) without further purification. $^{31}$P NMR (CDCl$_3$): δ 40.91 (s).

The PNH compound (6.4 g, 24.9 mmol) obtained above was added slowly to a stirred solution of PhPCl$_2$ (3.3 ml, 24.3 mmol) and triethylamine (6.8 ml, 48.9 mmol) in diethyl ether (150 ml) at 0° C. After complete addition, the reaction mixture was filtered through Celite and the volatiles removed in vacuo. A yellow, sticky oil was isolated and the oil was extracted with pentane. The pentane extract was filtered and evaporated in vacuo to give a thick clear oil of Ph$_2$PN(nBu)P(Cl)Ph, which solidified upon standing.

$^{31}$P NMR (CDCl$_3$): δ 139.24 (d, J=154.64 Hz), 65.34 (d, J=154.64 Hz).

Preparation of 2-[2-benzothiazolyloxy]iodobenzene

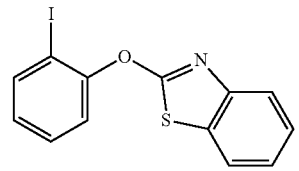 [SMILES: Ic1ccccc1Oc1nc2ccccc2s1]

A mixture of 2-bromobenzothiazole (2.0 g, 9.3 mmol), 2-iodophenol (2.16 g, 9.8 mmol) and potassium carbonate (2.6 g, 18.8 mmol) was stirred at 160° C. for 24 h in a sealed tube. At the end of the reaction the mixture was diluted with water and extracted with ethyl acetate. The organic extract was washed with 10% NaOH aqueous solution, dried over magnesium sulfate and the filtrate concentrated in vacuo to give a yellow viscous oil. The residue was purified by chromatography through a column of silica gel, eluting with ethyl acetate in n-hexane to afford the product after removal of the volatiles in vacuo. $^1$H NMR; δ (CDCl$_3$): 7.90 (dd, 1H, J=7.6 Hz and 1.4 Hz, aromatics,), 7.74-7.67 (br s, 1H, aromatics), 7.74-7.67 (br s, 1H, aromatics), 7.45-7.36 (m, 3H, aromatics), 7.30-7.27 (m, 1H, aromatics), 7.07-7.03 (m, 1H, aromatics).

Preparation of 2-[4-pyridyloxy]iodobenzene

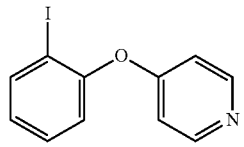 [SMILES: Ic1ccccc1Oc1ccncc1]

2-[4-pyridyloxy]iodobenzene was prepared using a similar procedure described above for the preparation of 2-[2-benzothiazolyloxy]iodobenzene using 4-chloropyridine hydrochloride (5.0 g, 33.6 mmol), 2-iodophenol (5.7 g, 25.9 mmol) and potassium carbonate (8.6 g, 62.3 mmol). $^1$H NMR δ (CDCl$_3$): 8.46 (d, 2H, J=5.6 Hz, aromatics,), 7.42 (t, 2H, J=8.0 Hz, aromatics,), 7.09 (d, 2H, aromatics, J=7.6 Hz), 6.83 (d, 2H, aromatics, J=6 Hz).

Preparation of 2-[4-pyridyloxy]phenylmagnesium iodide

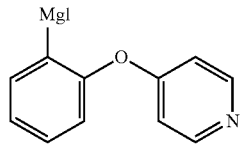

To a stirred solution of 2-[4-pyridyloxy]iodobenzene (976.2 mg, 3.3 mmol) in anhydrous THF (5 mL) at −40° C. was added iPrMgCl.LiCl (3.0 mL, 4.0 mmol, 1.3M in THF) solution. The reaction mixture was immediately warmed to 0° C. and stirred for a further 2 hours. The resultant phenylmagnesium iodide was used in the next step without further work up.

Preparation of 2-[methylsulfonyloxy]iodobenzene

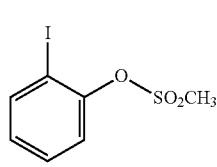 [SMILES: CS(=O)(=O)Oc1ccccc1I]

To a stirred solution of 2-iodophenol (5 g, 22.7 mmol) in anhydrous CH$_2$Cl$_2$ (100 ml), triethylamine (3.8 ml, 27.3 mmol) was added. The solution was cooled to 0° C. and methanesulfonyl chloride (2.8 ml, 36.3 mmol) was added. The reaction was stirred at 0° C. for 10 min and then for 22 h at room temperature. The mixture was diluted with H$_2$O (100 ml) and extracted with ethyl acetate. The organic phase was washed with brine and dried over anhydrous Mg$_2$SO$_4$, and the solvent was evaporated in vacuo to yield the product as yellow oil in high purity. $^1$H NMR; δ (CDCl$_3$): 7.9-7.88 (m, 1H, aromatics), 7.49-7.47 (m, 1H, aromatics), 7.44-7.40 (m, 1H, aromatics), 7.09-7.05 (m, 1H, aromatics), 3.32 (s, 3H, C$\underline{H}$$_3$SO$_2$O—).

Preparation of 2-[methylsulfonyloxy]phenylmagnesium iodide

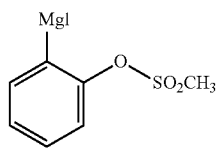

To a stirred solution of 2-[methylsulfonyloxy]iodobenzene (2.0 g, 6.7 mmol) in anhydrous THF (5 ml) at −40° C. was added iPrMgCl.LiCl (7.3 ml, 9.4 mmol, 1.3 M in THF). The reaction mixture was immediately warmed to 0° C. and stirred for a further 2 hours. The product was used in the next step without further purification.

Preparation of 2-hydroxy-3-iodobenzaldehyde (3-iodosalicylaldehyde)

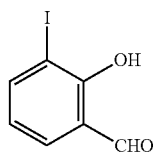

Triethylamine (25.2 ml, 182 mmol) was added to a stirred mixture of anhydrous magnesium chloride (17.3 g, 182 mmol) and paraformaldehyde (8.19 g, 272 mmol) in anhydrous THF (200 ml). 2-Iodophenol (20.0 g, 90.90 mmol) was added dropwise and the reaction was refluxed for 5 h. The reaction was cooled to room temperature and aqueous 1N HCl (100 ml) was added. The aqueous phase was extracted with ether (3×100 ml). The combined dark orange ether phase was filtered through a short silica column to give a pale yellow ether solution. Removal of the volatiles in vacuo afforded a bright yellow solid of the aldehyde product sufficiently pure for further synthetic use. $^1$H NMR δ (CDCl$_3$): 11.82 (s, 1H, OH), 9.77 (s, 1H, CHO), 8.01 (d, 1H, J=8.0 Hz, aromatics), 7.56 (d, 1H, J=8.0 Hz, aromatics), 6.86 (t, 1H, J=7.6 Hz, aromatics).

Preparation of 8-iodo-chromen-2-one

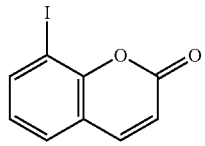

To a stirred solution of 3-iodosalicyladehyde (15.0 g, 60.5 mmol) in acetic anhydride (50 ml) was added potassium acetate (3.7 g, 24.2 mmol). The mixture was refluxed for 5 h. The reaction mixture was cooled to room temperature and diluted with ethyl acetate. The organic layer was washed with saturated aqueous NaCl, dried over magnesium sulfate and concentrated in vacuo. The residue was purified by silica chromatography, eluting with hexane:ethyl acetate (10:1) to give 8-iodo-chromen-2-one as a cream white solid. $^1$H NMR δ (CDCl$_3$): 7.98 (dd, 1H, J=8.0, 1.6 Hz), 7.64 (d, 1H, J=9 Hz, aromatics), 48 (dd, 1H, J=7.6, 1.6 Hz, aromatics), 7.06 (t, 1H, J=7.6 Hz, aromatics).

Preparation of (chromen-2-on-8-yl)(phenyl)phosphinechloride

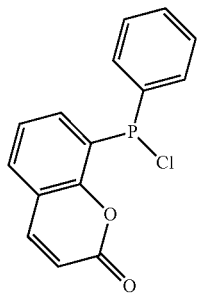 [SMILES: O=c1ccc2cccc(P(Cl)c3ccccc3)c2o1]

To a stirred solution of 8-iodo-chromen-2-one (1.0 g, 3.68 mmol) in anhydrous THF (10 mL) at −78° C. was added iPrMgCl.LiCl (4.2 ml, 5.5 mmol, 1.3 M in THF) solution. The reaction mixture was immediately warmed to 0° C. and stirred for a further 30 min. The reaction mixture was slowly added to a solution of PhPCl$_2$ (0.66 g, 3.68 mmol) in anhydrous THF (15 ml) at −78° C. After addition was complete, the suspension was immediately allowed to warm to room temperature and then stirred at room temperature for a further 20 min after which the reaction was complete as judged by $^{31}$P NMR (CDCl$_3$): δ 71.12 (s).

Preparation of (2-fluorophenyl)phenyl)phosphine chloride

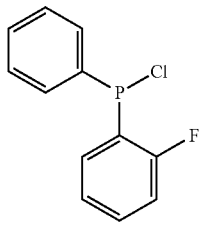 [SMILES: Fc1ccccc1P(Cl)c1ccccc1]

A dry and argon flushed Schlenk was charged with iPrMgCl.LiCl (1.42 g, 7.5 mmol, 1.3 M solution in THF). The solution was cooled in an ice bath and 1-bromo-2-fluorobenzene (1.31 g, 7.5 mmol) was added dropwise. The reaction mixture was stirred for 1 hr and the resulting Grignard reagent was slowly added to a solution of anhydrous THF (10 ml) of PhPCl$_2$ (1.34 g, 7.5 mmol) at −78° C. After addition was complete, the suspension was stirred at room temperature for a further 1 h after which the reaction was complete as judged by $^{31}$P NMR (CDCl$_3$): δ 71.2 (d, J=66.0 Hz).

Preparation of (2-methoxyphenyl)(phenyl)phosphine chloride

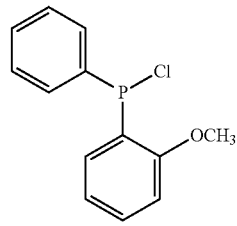 [SMILES: COc1ccccc1P(Cl)c1ccccc1]

1-Bromo-2-methoxybenzene (2.0 g, 10.7 mmol) was added to a mixture of magnesium turnings (0.3 g, 12.8 mmol) in anhydrous THF (20 ml). A vigorous reaction ensued. Stirring was continued at room temperature. Once the reaction exotherm had dissipated, the reaction mixture was used for the next step as described below:

The Grignard reagent (separated from excess Mg) was incrementally added to a solution of PhPCl$_2$ (1.5 mL, 10.7 mmol) in anhydrous THF (30 ml) at −78° C. After addition was complete, the suspension was stirred at room temperature for a further 15 min after which the reaction was complete as judged by $^{31}$P NMR. The product was used in the next step without isolation. $^{31}$P NMR (CDCl$_3$): δ 77.07 (s); 68.80 (s).

Preparation of (2-[trifluoromethoxy]phenyl)(phenyl)PN(iPr)P(phenyl)$_2$

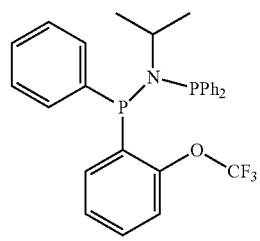

PNH formation: isopropylamine (0.14 g, 2.36 mmol) and Et$_3$N (0.47 ml, 4.60 mmol) were added to the crude (2-[trifluoromethoxy]phenyl)(phenyl)phosphine chloride (0.71 g, 2.33 mmol) [prepared as described above] in diethyl ether (50 ml) resulting in immediate formation of a white precipitate. The reaction mixture was stirred at room temperature until complete formation of the PNH intermediate as judged by $^{31}$P NMR analysis. The suspension was filtered through a short column of activated alumina to give the ether solution of the desired PNH product in reasonable purity. The solvent was removed in vacuo to give the PNH compound, (2-[trifluoromethoxy]phenyl)(phenyl)PN(iPr)H. $^{31}$P NMR (CDCl$_3$): δ 26.2 (d, J=5.7 Hz).

PNP formation: The PNH molecule described above (0.64 g, 1.96 mmol) was re-dissolved in DCM (5 ml). Et$_3$N (0.40 ml, 3.94 mmol) was added, followed by an incremental addition of Ph$_2$PCl (0.43 g, 1.96 mmol) at room temperature. After complete conversion of the PNH (judged by $^{31}$P NMR analysis) to the PNP, the volatiles were removed in vacuo. Ether (100 ml) was added and the resultant suspension was filtered through a short column of activated alumina to give the desired PNP upon solvent removal. $^{31}$P NMR (CDCl$_3$): δ 52.4 (br s), 34.1 (br s).

Preparation of (2-[trifluoromethoxy]phenyl)(phenyl) PN(nBu)P(phenyl)$_2$

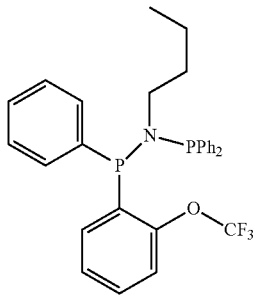

PNH formation: n-butylamine (1.1 g, 15.0 mmol) and Et$_3$N (1.50 ml, 10.78 mmol) were added to the crude (2-[trifluoromethoxy]phenyl)(phenyl)phosphine chloride (1.0 g, 3.41 mmol) in diethyl ether (50 ml) resulting in immediate formation of a white precipitate. The reaction mixture was stirred at room temperature until complete formation of the PNH intermediate as judged by $^{31}$P NMR analysis. The suspension was filtered through a short column of activated alumina to give the ether solution of the desired PNH product in reasonable purity. The solvent was removed in vacuo to give the PNH compound, (2-[trifluoromethoxy] phenyl)(phenyl)PN(nBu)H. 31P NMR (CDCl$_3$): δ 32.1 (s).

PNP formation: The PNH molecule described above (1.1 g, 3.0 mmol) was re-dissolved in DCM (5 ml). Et$_3$N (0.65 ml, 4.6 mmol) was added, followed by addition of Ph$_2$PCl (0.65 g, 3.0 mmol) at room temperature. After complete conversion of the PNH (as judged by $^{31}$P NMR analysis) to the PNP, the volatiles were removed in vacuo. Ether (100 ml) was added and the resultant mixture was filtered through a short column of activated alumina to give the desired PNP upon solvent removal. $^{31}$P NMR (CDCl$_3$): δ 62.3 (br s), 52.3.3 (br s).

Preparation of (2-[trifluoromethoxy]phenyl)(phenyl) PN(nBu)P(2-[trifluoromethoxy]phenyl)(phenyl)

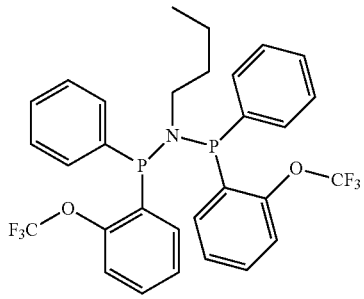 [SMILES: CCCCN(P(c1ccccc1)c1ccccc1OC(F)(F)F)P(c1ccccc1)c1ccccc1OC(F)(F)F]

PNP formation: n-butylamine (108 mg, 1.47 mmol) and Et$_3$N (0.82 ml, 5.90 mmol) were added to the crude (2-[trifluoromethoxy]phenyl)(phenyl)phosphine chloride (0.90 g, 3.0 mmol) in dichloromethane (5 ml). The reaction mixture was stirred at room temperature. After complete conversion of the PCl (as judged by $^{31}$P NMR analysis) to the PNP, the volatiles were removed in vacuo. Ether (100 ml) was added and the resultant mixture was filtered through a short column of activated alumina to give the desired PNP upon solvent removal. $^{31}$P NMR (CDCl$_3$): δ 52.9 (br s), 51.4 (br s).

Preparation of (2-[trifluorothiomethoxy]phenyl) (phenyl)PN(nBu)P(phenyl)$_2$

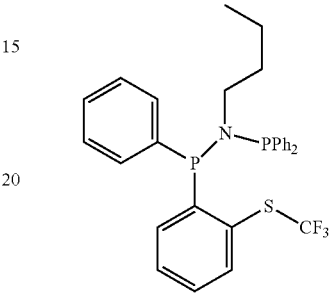

PNP formation: To a stirred solution of 2-bromo-trifluorothiomethoxybenzene (0.89 g, 3.3 mmol) in anhydrous THF (5 ml) at 0° C. was added isopropylmagnesium lithium chloride complex (3.76 ml, 1.3 M in THF, 5.0 mmol). The solution was stirred at 0° C. for 2 hours. The resulting 2-trifluorothiomethoxyphenylmagnesium halide solution was added to a stirred solution of Ph$_2$PN(nBu)PPhCl (1.3 g, 3.25 mmol) in anhydrous THF (10 mL) at −78° C. The reaction mixture was left to warm to room temperature and the THF was removed in vacuo. The residue was slurried in diethyl ether (80 ml) and the mixture was filtered through a short alumina column. The filtrate was evaporated in vacuo to afford the desired PNP. $^{31}$P NMR (CDCl$_3$): δ 63.0 (br s), 54.2 (br s).

Preparation of (2-[4-pyridyloxy]phenyl)(phenyl)PN (nBu)P(phenyl)$_2$

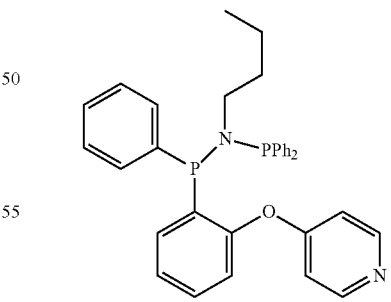

PNP formation: The PNP compound was synthesized from the reaction of a slight excess of Ph$_2$PN(nBu)PPhCl (2.0 g, 5.0 mmol) and 2-[4-pyridyloxy]phenyl magnesium iodide (976.2 mg, 3.3 mmol)] following the typical procedure described for (2-[trifluorothiomethoxy]phenyl)(phenyl)PN(nBu)P(phenyl)$_2$.

$^{31}$P NMR (CDCl$_3$): δ 72.41 (br s,), 53.96 (br s).

Preparation of (2-[2-benzothiazolyloxy]phenyl)(phenyl)PN(nBu)P(phenyl)$_2$

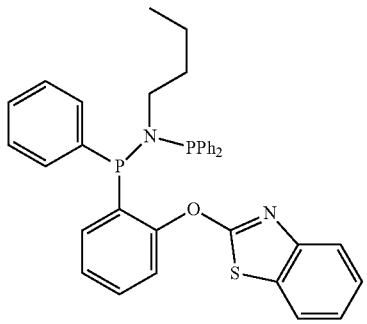

PNH formation: To a stirred solution of 2-[2-benzothiazolyloxy]iodobenzene (2.2 g, 6.2 mmol) in anhydrous THF (5 mL) at −40° C. was added iPrMgCl.LiCl (6.7 ml, 8.7 mmol, 1.3 M in THF) solution. The reaction mixture was immediately warmed to 0° C. and stirred for a further 2 hours. The resultant phenylmagnesium iodide was slowly added to a solution of PhPCl$_2$ (0.92 g, 5.2 mmol) in anhydrous THF (20 ml) at −78° C. After the addition was complete, the reaction was stirred at room temperature for a further 1 h. This was followed by addition of n-butylamine (0.92 g, 12.40 mmol) and Et$_3$N (1.70 ml, 12.4 mmol) resulting in immediate formation of a white precipitate. The reaction mixture was stirred at room temperature until complete formation of the PNH intermediate as judged by $^{31}$P NMR analysis. The suspension was filtered through a short column of activated alumina to give the ether solution of the desired PNH product in reasonable purity. The solvent was removed in vacuo to give the PNH compound, (2-[2-benzothiazolyloxy]phenyl)(phenyl)PN(nBu)H. $^{31}$P NMR (CDCl$_3$): δ 49.1 (s).

PNP formation: The PNH molecule described above (2.0 g, 4.9 mmol) was re-dissolved in DCM (10 mil). Et$_3$N (1.1 ml, 7.8 mmol) was added, followed by addition of Ph$_2$PCl (1.07 g, 4.9 mmol) at room temperature. After complete conversion of the PNH (as judged by $^{31}$P NMR analysis) to the PNP, the volatiles were removed in vacuo. Ether (100 ml) was added and the resultant mixture was filtered through a short column of activated alumina to give the desired PNP upon solvent removal. $^{31}$P NMR (CDCl$_3$): δ 72.42 (d, J=49.3 Hz), 54.00 (d, J=45.7 Hz).

Preparation of (2-[methylsulfonyloxy]phenyl)(phenyl)PN nBu)P(phenyl)$_2$

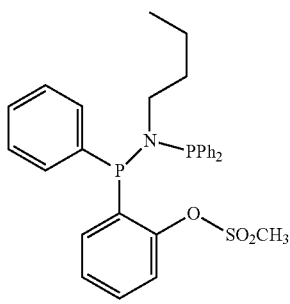

PNP formation: The PNP compound was synthesized from the reaction of Ph$_2$PN(nBu)PPhCl (2.0 g, 5.0 mmol) and 2-[methylsulfonyloxy]phenyl magnesium iodide (2.0 g, 6.7 mmol)] following the typical procedure described for PNP molecule (2-[trifluorothiomethoxy]phenyl)(phenyl)PN(nBu)P(phenyl)$_2$. $^{31}$P NMR (CDCl$_3$): δ 55.63 (d, J=14.6 Hz), 46.54 (d, d, J=14.6 Hz).

Preparation of (chromen-2-one-8-yl)(phenyl)PN(nBu)P(phenyl)$_2$

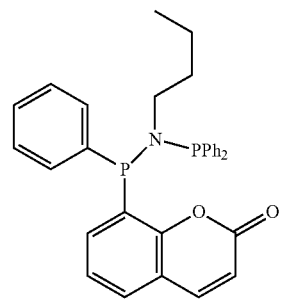

PNH formation: The synthesis of Ph$_2$PN(nBu)H has been described above for the synthesis of Ph$_2$N(nBu)PPhCl.

PNP formation: The PNH, Ph$_2$PN(nBu)H molecule (0.49 g, 1.73 mmol) was dissolved in DCM (10 ml). Et$_3$N (0.35 g, 3.46 mmol) was added, followed by addition of (chromen-2-on-8-yl)(phenyl)PCl (500 mg, 1.73 mmol) at room temperature. After complete conversion of PCl (as judged by $^{31}$P NMR analysis) to the PNP, the volatiles were removed in vacuo. Ether (100 ml) was added and the resultant mixture was filtered through a short column of activated alumina to give the desired PNP upon solvent removal. $^{31}$P NMR (CDCl$_3$): δ 60.8 (br s), 49.1 (br s).

Preparation of (2-fluorophenyl)phenyl)PN(iPr)P(phenyl)$_2$

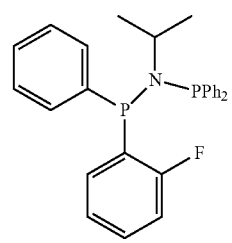

PNH formation: isopropylamine (0.30 g, 5.01 mmol) and Et$_3$N (1.01 ml, 10.02 mmol) were added to the crude (2-fluorophenyl)(phenyl)phosphine chloride (1.10 g, 5.01 mmol) in diethyl ether (50 ml) resulting in immediate formation of a white precipitate. The reaction mixture was stirred at room temperature until complete formation of the PNH intermediate as judged by $^{31}$P NMR analysis. The suspension was filtered through a short column of activated alumina to give the ether solution of the desired PNH product in reasonable purity. The solvent was removed in vacuo to give the PNH compound, (2-fluorophenyl)(phenyl)PN(iPr)H. $^{31}$P NMR (CDCl$_3$): δ 26.2 (d, J=5.7 Hz).

PNP formation: The PNH molecule described above (1.19 g, 4.55 mmol) was re-dissolved in DCM (5 ml). Et$_3$N (0.92 g, 9.12 mmol) was added, followed by addition of Ph$_2$PCl (0.92 g, 4.55 mmol) at room temperature. After complete conversion of the PNH (as judged by $^{31}$P NMR analysis) to the PNP, the volatiles were removed in vacuo. Ether (100 ml) was added and the resultant mixture was filtered through a short column of activated alumina to give the desired PNP upon solvent removal. $^{31}$P NMR (CDCl$_3$): δ 51.1 (br s), 35.7 (br s).

Preparation of (phenyl)PN(iPr)P(phenyl)$_2$

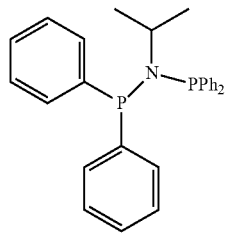

This compound was prepared from the reaction of isopropylamine (1.0 g, 16.9 mmol), Et$_3$N (3.4 g, 33.8 mmol), Ph$_2$PCl (7.4 g, 33.8 mmol) in DCM, following a procedure described in *Synthesis*, 2007, 24, 3863. $^{31}$P NMR (CDCl$_3$): δ 48.2 (s).

Preparation of (2-methoxyphenyl)(phenyl)PN(i-Pr)P(phenyl)$_2$

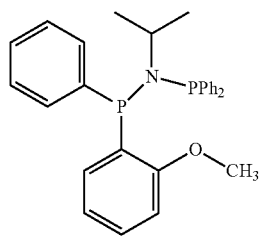

PNH formation: isopropylamine (0.51 g, 5.98 mmol) and Et$_3$N (1.64 ml, 11.96 mmol) were added to the crude (2-methoxyphenyl)(phenyl)phosphine chloride (1.50 g, 5.98 mmol) in diethyl ether (50 ml) resulting in immediate formation of a white precipitate. The reaction mixture was stirred at room temperature until complete formation of the PNH intermediate as judged by $^{31}$P NMR analysis. The suspension was filtered through a short column of activated alumina to give the ether solution of the desired PNH product in reasonable purity. The solvent was removed in vacuo to give the PNH compound, (2-methoxyphenyl)(phenyl)PN(iPr)H. $^{31}$P NMR (CDCl$_3$): δ 28.6 (s).

PNP formation: The PNH molecule described above (1.63 g, 5.98 mmol) was re-dissolved in DCM (5 ml). Et$_3$N (1.81 ml, 13.18 mmol) was added, followed by addition of Ph$_2$PCl (1.31 g, 5.98 mmol) at room temperature. After complete conversion of the PNH (as judged by $^{31}$P NMR analysis) to the PNP, the volatiles were removed in vacuo. Ether (100 ml) was added and the resultant mixture was filtered through a short column of activated alumina to give the desired PNP upon solvent removal. $^{31}$P NMR (CDCl$_3$): δ 52.4 (br s), 35.3 (br s).

Preparation of (2-methoxyphenyl)(phenyl)PN(n-Bu)P(phenyl)$_2$

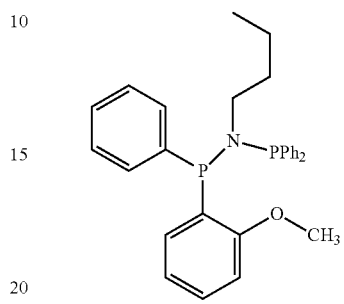

PNH formation: n-butylamine (1.7 g, 23.1 mmol) and Et$_3$N (3.2 ml, 23.1 mmol) were added to the crude (2-methoxyphenyl)(phenyl)PCl (2.90, 11.6 mmol) [prepared as described above] in diethyl ether (50 ml) resulting in immediate formation of a white precipitate. The reaction mixture was stirred at room temperature until complete formation of the PNH intermediate as judged by $^{31}$P NMR analysis. The suspension was filtered through a short column of activated alumina to give the ether solution of the desired PNH product in reasonable purity. The solvent was removed in vacuo to give the PNH compound, PNH ((2-methoxyphenyl)(phenyl)PN(n-Bu)H). $^{31}$P NMR (CDCl$_3$): δ 34.82 (s).

PNP formation: To a DCM (5 ml) solution of (2-methoxyphenyl)(phenyl)N(Bu)H (2.4 g, 8.5 mmol) and Et$_3$N (1.4 ml, 10.2 mmol) was added ClPPh$_2$ (1.58 g, 8.5 mmol). The reaction was left to stir overnight. The solvent was then removed in vacuo and the residue re-slurried in ether (100 ml), followed by filtration of the solids and removal of the solvent in vacuo to give a clear yellowish oil. $^{31}$P NMR; δ (CDCl$_3$): 61.42 (d, J=35.34 Hz); 52.28 (d, J=35.99 Hz).

Example 1

Ethylene Tetramerisation with (2-[Trifluoromethoxy]Phenyl)(Phenyl)PN(iPr)P(Phenyl)$_2$ at 60° C. and 45 Bar A 600 ml stainless steel reactor was heated to 1200° C. for 30 minutes under vacuum, backfilled with N$_2$ and then cooled to 60° C. The reactor was charged with 2,2,4-trimethylpentane (TMP) (100 ml), and heated to 60° C. Separately, MMAO-3A (2.4 mmol Al) was added to a mixture of Cr(acac)$_3$ (2.5 μmol) and (2-[trifluoromethoxy]phenyl)(phenyl)PN(iPr)P(phenyl)$_2$ (2.5 μmol) in methylcyclohexane (5 ml). This mixture was then transferred to the reactor. The reactor was pressurised with ethylene (45 bar), and stirred (1300 r.p.m.) with a gas entraining stirrer. The temperature in the reactor increased to 62-65° C., at which point the reactor was cooled by means of an internal cooling coil to maintain a constant temperature of 60° C. throughout the run. The reaction pressure was kept constant throughout the run by feeding ethylene on demand, and the consumption of ethylene was monitored via a flow meter. At the conclusion of the run after 10 minutes and 160 g total ethylene uptake (including the ethylene required to pressurise the reactor), the reactor was rapidly cooled to 5° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Example 2

Ethylene Tetramerisation with (2-[Trifluoromethoxy]Phenyl)(Phenyl)PN(iPr)P(Phenyl)$_2$ at 60° C. and 45 Bar The procedure of example 1 was followed, except that 0.625 μmol Cr(acac)$_3$, 0.625 μmol (2-[trifluoromethoxy]phenyl)(phenyl)PN(iPr)P(phenyl)$_2$ and 0.6 mmol Al in MMAO-3A was used, and the reaction was terminated after 16 minutes and 160 g total ethylene uptake.

Example 3

Ethylene Tetramerisation with (2-[Trifluoromethoxy]Phenyl)(Phenyl)PN(nBu)P(Phenyl) at 60° C. and 45 Bar The procedure of example 1 was followed, except that 1.25 μmol Cr(acac)$_3$, 1.25 μmol of the ligand (2-[trifluoromethoxy]phenyl)(phenyl)PN(nBu)P(phenyl)$_2$ and 1.2 mmol Al in MMAO-3A was used, and the reaction was terminated after 30 minutes and 160 g total ethylene uptake.

Example 4

Ethylene Tetramerisation with (2-[Trifluoromethoxy]phenyl)(Phenyl)PN(nBu)P(Phenyl) at 100° C. and 45 Bar The procedure of example 1 was followed, except that the ligand (2-[trifluoromethoxy]phenyl)(phenyl)PN(nBu)P(phenyl)$_2$ (2.5 μmol) was used, 200 ml of TMP was used, the reaction temperature was maintained at 100° C. and the reaction was terminated after 20 minutes and 113 g ethylene uptake. The results are shown in Table 1.

Example 5

Ethylene Tetramerisation with (2-[Trifluoromethoxy]Phenyl)(Phenyl)PN(nBu)P(Phenyl) at 90° C. and 60 Bar The procedure of example 1 was followed, except that the ligand (2-[trifluoromethoxy]phenyl)(phenyl)P N(nBu)P(phenyl)$_2$ (2.5 μmol) was used, 200 ml of MCH was used (instead of TMP), the reaction temperature was maintained at 90° C., the reaction pressure was maintained at 60 bar, and the reaction was terminated after 10 minutes and 150 g ethylene uptake. The results are shown in Table 1.

Example 6

Ethylene Tetramerisation with (2-[Trifluoromethoxy]Phenyl)(Phenyl)PN(nBu)P(2-[Trifluoromethoxy]Phenyl) (Phenyl) at 60° C. and 45 Bar The procedure of example 1 was followed, except that ligand (2-[trifluoromethoxy]phenyl)(phenyl)PN(nBu)P(2-[trifluoromethoxy]phenyl) (phenyl) (2.5 μmol) was used and the reaction was terminated after 10.7 minutes and 160 g ethylene uptake. The results are shown in Table 1.

Example 7

Ethylene Tetramerisation with (2-[Trifluorothiomethoxy]Phenyl)(Phenyl)PN(nBu)P(phenyl), at 60° C. and 45 Bar The procedure of example 1 was followed, except that the ligand (2-[trifluorothiomethoxy]phenyl)(phenyl)PN(nBu)P(phenyl)$_2$ (2.5 μmol) was used and the reaction was terminated after 30 minutes and 62 g ethylene uptake. The results are shown in Table 1.

Example 8

Ethylene Tetramerisation with (2-[4-Pyridyloxy]Phenyl)(Phenyl)PN(nBu)P(Phenyl)$_2$ at 60° C. and 45 Bar The procedure of example 1 was followed, except that the ligand (2-[4-pyridyloxy]phenyl)(phenyl)PN(nBu)P(phenyl)$_2$ (2.5 μmol) was used and the reaction was terminated after 29.1 minutes and 160 g ethylene uptake. The results are shown in Table 1.

Example 9

Ethylene Tetramerisation with (2-[2-Benzothiazolyloxy]Phenyl)(Phenyl)PN(nBu)P(Phenyl)$_2$ at 60° C. and 45 Bar The procedure of example 1 was followed, except that the ligand (2-[2-benzothiazolyloxy]phenyl)(phenyl)PN(nBu)P(phenyl)$_2$ (2.5 μmol) was used and the reaction was terminated after 19.5 minutes and 160 g ethylene uptake. The results are shown in Table 1.

Example 10

Ethylene Tetramerisation with (2-[Methylsulfonyloxy]Phenyl)(Phenyl)PN(nBu)P(Phenyl)$_2$ at 60° C. and 45 Bar The procedure of example 1 was followed, except that the ligand (2-[methylsulfonyloxy]phenyl)(phenyl)PN(nBu)P(phenyl)$_2$ (2.5 μmol) was used and the reaction was terminated after 26 minutes and 53 g ethylene uptake. The results are shown in Table 1.

Example 11

Ethylene Tetramerisation with (Chromen-2-on-8-Yl)(Phenyl)PN(nBu)P(Phenyl)$_2$ at 60° C. and 45 Bar The procedure of example 1 was followed, except that the ligand (chromen-2-on-8-yl)(phenyl)PN(nBu)P(phenyl)$_2$ (2.5 μmol) was used and the reaction was terminated after 30 minutes and 60 g ethylene uptake. The results are shown in Table 1.

Comparative Example 1

Ethylene tetramerisation with (2-Fluorophenyl)(Phenyl)PN(iPr)P(Phenyl) at 60° C. and 45 Bar The procedure of example 1 was followed, except that the ligand (2-fluorophenyl)(phenyl)PN(iPr)P(phenyl)$_2$ (2.5 µmol) was used and the reaction was terminated after 11 minutes and 160 g ethylene uptake. The results are shown in Table 1.

Comparative Example 2

Ethylene Tetramerisation with (Phenyl)$_2$PN(iPr)P(Phenyl) at 60° C. and 45 Bar The procedure of example 1 was followed, except that the ligand (phenyl)$_2$PN(iPr)P(phenyl)$_2$ (2.5 µmol) was used and the reaction was terminated after 34.5 minutes and 160 g ethylene uptake. The results are shown in Table 1.

Comparative Example 3

Ethylene Tetramerisation with (2-Methoxyphenyl)(Phenyl)PN(iPr)P(Phenyl)$_2$ at 60° C. and 45 Bar The procedure of example 1 was followed, except that ligand (2-methoxyphenyl)(phenyl)PN(iPr)P(phenyl)$_2$ (2.5 µmol) was used and the reaction was terminated after 62 minutes and 160 g ethylene uptake. The results are shown in Table 1.

Comparative Example 4

Ethylene Tetramerisation with (2-Methoxyphenyl)(Phenyl)PN(nBu)P(Phenyl) at 60° C. and 45 Bar The procedure of example 1 was followed, except that ligand (2-methoxyphenyl)(phenyl)PN(nBu)P(phenyl)$_2$ (2.5 µmol) was used and the reaction was terminated after 16.2 minutes and 160 g ethylene uptake. The results are shown in Table 1.

Comparative Example 5

Ethylene Tetramerisation with (2-Methoxyphenyl)(Phenyl)PN(nBu)P(Phenyl) at 100° C. and 45 Bar The procedure of example 1 was followed, except that ligand (2-methoxyphenyl)(phenyl)PN(nBu)P(phenyl)$_2$ (2.5 µmol) was used, 200 ml of TMP was used, the reaction temperature was maintained at 100° C. and the reaction was terminated after 8 minutes and 150 g ethylene uptake. The results are shown in Table 1.

TABLE 1

| Example | Ligand | Temp (° C.), Press. (bar) | Activity (×10$^6$ g/gCr/h) |
|---|---|---|---|
| 1 | (2-[trifluoromethoxy]phenyl)(phenyl)PN(iPr)P(phenyl)$_2$ | 60, 45 | 5.8 |
| 2 | (2-[trifluoromethoxy]phenyl)(phenyl)PN(iPr)P(phenyl)$_2$ | 60, 45 | 12.4 |
| 3 | (2-[trifluoromethoxy]phenyl)(phenyl)PN(nBu)P(phenyl)$_2$ | 60, 45 | 3.3 |
| 4 | (2-[trifluoromethoxy]phenyl)(phenyl)PN(nBu)P(phenyl)$_2$ | 100, 45 | 1.6 |
| 5 | (2-[trifluoromethoxy]phenyl)(phenyl)PN(nBu)P(phenyl)$_2$ | 90, 60 | 4.3 |
| 6 | (2-[trifluoromethoxy]phenyl)(phenyl)PN(nBu)P(2-[trifluoromethoxy]phenyl)(phenyl) | 60, 45 | 4.5 |
| 7 | (2-[trifluorothiomethoxy]phenyl)(phenyl)PN(nBu)P(phenyl)$_2$ | 60, 45 | 0.2 |
| 8 | (2-[4-pyridyloxy]phenyl)(phenyl)PN(nBu)P(phenyl)$_2$ | 60, 45 | 1.7 |
| 9 | (2-[2-benzothiazolyloxy]phenyl)(phenyl)PN(nBu)P(phenyl)$_2$ | 60, 45 | 2.4 |
| 10 | (2-[methylsulfonyloxy]phenyl)(phenyl)PN(nBu)P(phenyl)$_2$ | 60, 45 | 0.08 |
| 11 | (chromen-2-on-8-yl)(phenyl)PN(nBu)P(phenyl)$_2$ | 60, 45 | 0.34 |
| Comp 1 | (2-fluorophenyl)(phenyl)PN(iPr)P(phenyl)$_2$ | 60, 45 | 5.1 |
| Comp 2 | (phenyl)$_2$PN(iPr)P(phenyl)$_2$ | 60, 45 | 1.5 |
| Comp 3 | (2-methoxyphenyl)(phenyl)PN(iPr)P(phenyl)$_2$ | 60, 45 | 0.8 |
| Comp 4 | (2-methoxyphenyl)(phenyl)PN(nBu)P(phenyl)$_2$ | 60, 45 | 4.1 |
| Comp 5 | (2-methoxyphenyl)(phenyl)PN(nBu)P(phenyl)$_2$ | 100, 45 | 6.8 |

| Example | 1-Hexene selectivity (mass %) | C6 cyclics selectivity (mass %) | 1-Octene selectivity (mass %) | C10-C30 selectivity (mass %) | Polymer selectivity (mass %) | 1-Octane:1-Hexene ratio (g/g) |
|---|---|---|---|---|---|---|
| 1 | 33.0 | 3.9 | 53.3 | 8.7 | 0.4 | 1.62 |
| 2 | 35.3 | 3.8 | 51.6 | 8.5 | 0.1 | 1.46 |
| 3 | 18.4 | 9.7 | 57.8 | 9.9 | 1.2 | 3.14 |
| 4 | 49.7 | 4.4 | 33.2 | 6.3 | 5.5 | 0.67 |
| 5 | 43.8 | 5.6 | 39.1 | 6.8 | 3.6 | 0.89 |
| 6 | 28.8 | 6.8 | 52.9 | 8.9 | 0.85 | 1.84 |
| 7 | 29.5 | 5.8 | 31.5 | 5.1 | 22.2 | 1.07 |
| 8 | 18.5 | 4.0 | 65.6 | 9.6 | 1.4 | 3.54 |
| 9 | 18.2 | 2.6 | 67.0 | 10.4 | 0.80 | 3.69 |
| 10 | 25.6 | 5.1 | 36.8 | 7.0 | 23.3 | 1.44 |
| 11 | 19.2 | 9.2 | 43.4 | 11.7 | 11.4 | 1.46 |

TABLE 1-continued

| | | | | | | |
|---|---|---|---|---|---|---|
| Comp 1 | 29.1 | 1.9 | 53.2 | 14.9 | 0.3 | 1.81 |
| Comp 2 | 14.0 | 4.1 | 68.9 | 11.9 | 0.4 | 4.92 |
| Comp 3 | 55.0 | 0.3 | 10.9 | 28.8 | 3.7 | 0.20 |
| Comp 4 | 55.5 | 2.2 | 24.4 | 16.5 | 0.4 | 0.43 |
| Comp 5 | 78.8 | 0.5 | 6.2 | 12.8 | 0.3 | 0.08 |

The invention claimed is:

1. A process for the oligomerisation of ethylene to predominantly 1-hexene or 1-octene or mixtures of 1-hexene and 1-octene, the process including contacting ethylene with a catalyst under ethylene oligomerisation conditions, said catalyst comprising:
   i) a source of chromium;
   ii) a ligating compound of the formula

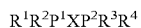

wherein $P^1$ and $P^2$ are phosphorus atoms;
   X is a linking group between $P^1$ and $P^2$; and
   $R^1$ to $R^4$ are independently a hydrocarbyl group, an organoheteryl group or a heterohydrocarbyl group, wherein at least one of $R^1$, $R^2$, $R^3$, and $R^4$ includes a substituted aromatic ring directly bonded to $P^1$ or $P^2$ and which is substituted at a ring atom adjacent to the ring atom bonded to $P^1$ or $P^2$ with a substituent Y, where Y can be represented as:

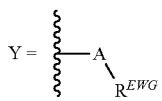

such that A is selected from the group consisting of O, S and $NR^5$, where $R^5$ is a hydrocarbyl, heterohydrocarbyl or organoheteryl group; and
   $R^{EWG}$ is an electron withdrawing group; and
   iii) optionally a catalyst activator or combination of catalyst activators.

2. The process as claimed in claim 1, wherein $R^1$ to $R^4$ all include aromatic or heteroaromatic moieties directly bonded to $P^1$ or $P^2$.

3. The process as claimed in claim 1, wherein at least one of the $R^1$ to $R^4$ groups is a substituted phenyl group and all of the remaining $R^1$ to $R^4$ groups are optionally substituted phenyl groups.

4. The process according to claim 1, wherein the Y-substituted aromatic rings of the $R^1$ to $R^4$ groups are selected from a group consisting of phenyl, pyridyl, furyl, thiophenyl, imidazolyl, pyrazolyl and oxazolyl.

5. The process according to claim 1, wherein the Y-substituted aromatic rings are phenyl groups, in which the Y substituent will be at the ortho position relative to the carbon ring atom bonded to $P^1$ or $P^2$.

6. The process according to claim 1, wherein A is O or S.

7. The process according to claim 1, wherein $R^{EWG}$ has a Hammett $\sigma_p$ value of greater than +0.15.

8. The process according to claim 1, wherein $R^{EWG}$ is selected from a group comprising halogen-substituted alkyl, halogen-substituted cycloalkyl, halogen-substituted aryl, heteroaryl, $-SO_2R^6$, $-(C=O)R^6$, $-CN$; where $R^6$ is a hydrogen, a hydrocarbyl group, or a heterohydrocarbyl group.

9. The process according to claim 1, wherein $R^{EWG}$ is selected from a group comprising halogen-substituted alkyl, halogen-substituted cycloalkyl, halogen-substituted aryl and heteroaryl.

10. The process according to claim 1, wherein $R^{EWG}$ is selected from a group comprising fluorine-substituted alkyl, fluorine-substituted cycloalkyl and fluorine-substituted aryl.

11. The process according to claim 1, wherein $R^{EWG}$ is a fluorine-substituted alkyl such that at least one fluorine atom is bonded to the carbon atom bonded to A.

12. The process according to claim 1, wherein $R^{EWG}$ is selected from a group comprising fluoromethyl; difluoromethyl; trifluoromethyl; 1,1'-difluoroethyl; chlorodifluoromethyl; pentafluoroethyl; heptafluoropropyl; nonafluorobutyl, and the like.

13. The process according to claim 1, wherein $R^{EWG}$ is trifluoromethyl.

14. The process according to claim 1, wherein no more than two of $R^1$ to $R^4$ includes a substituted aromatic ring with the Y substituent.

15. The process according to claim 1, wherein only one of $R^1$, $R^2$, $R^3$, and $R^4$ includes a substituted aromatic ring with the Y substituent.

* * * * *